(12) United States Patent
Bhirud Shekhar et al.

(10) Patent No.: US 8,912,325 B2
(45) Date of Patent: Dec. 16, 2014

(54) PROCESS FOR PREPARATION OF IMATINIB AND ITS MESYLATE SALT

(75) Inventors: Bhaskar Bhirud Shekhar, Punjab (IN); Kumar Jain Anshul, Punjab (IN); Kumar Sharma Ajay, Punjab (IN)

(73) Assignee: Ind-Swift Laboratories Limited, Chandigarh, IN (US)

( * ) Notice: Subject to any disclaimer, the term of this patent is extended or adjusted under 35 U.S.C. 154(b) by 0 days.

(21) Appl. No.: 14/008,727

(22) PCT Filed: Mar. 27, 2012

(86) PCT No.: PCT/IN2012/000202
§ 371 (c)(1),
(2), (4) Date: Sep. 30, 2013

(87) PCT Pub. No.: WO2012/131711
PCT Pub. Date: Oct. 4, 2012

(65) Prior Publication Data
US 2014/0221652 A1    Aug. 7, 2014

(30) Foreign Application Priority Data
Mar. 31, 2011    (IN) .............................. 926/DEL/2011

(51) Int. Cl.
*C07D 401/04*    (2006.01)
*C07C 309/04*    (2006.01)

(52) U.S. Cl.
CPC ............ *C07D 401/04* (2013.01); *C07C 309/04* (2013.01)
USPC ........................................................ 544/295

(58) Field of Classification Search
USPC ........................................................ 544/295
See application file for complete search history.

(56) References Cited

U.S. PATENT DOCUMENTS

| | | |
|---|---|---|
| 5,521,184 A | 5/1996 | Zimmerman |
| 6,894,051 B1 | 5/2005 | Zimmerman et al. |
| 7,507,821 B2 | 3/2009 | Anli et al. |
| 7,544,799 B2 | 6/2009 | Zimmerman et al. |
| 7,550,591 B2 | 6/2009 | Xing et al. |
| 7,638,627 B2 | 12/2009 | Kankan et al. |
| 7,732,601 B2 | 6/2010 | Szczepek et al. |
| RE43,932 E | 1/2013 | Zimmerman et al. |
| 2006/0223816 A1 | 10/2006 | Adin et al. |
| 2007/0197545 A1 | 8/2007 | Szczepek et al. |
| 2007/0265288 A1 | 11/2007 | Pathi et al. |
| 2008/0090833 A1 | 4/2008 | Jegorov et al. |
| 2008/0103305 A1 | 5/2008 | MacDonald et al. |
| 2008/0255138 A1 | 10/2008 | Amala et al. |
| 2012/0309767 A1 | 12/2012 | Ashwani et al. |

FOREIGN PATENT DOCUMENTS

| | | |
|---|---|---|
| CN | 101641345 | 2/2010 |
| CN | 101735196 | 6/2010 |
| CN | 102040587 | 5/2011 |
| IN | 2009KO00216 | 8/2010 |
| WO | 2004074502 | 9/2004 |
| WO | 2006048890 | 5/2006 |
| WO | 2008024829 | 2/2008 |
| WO | 2008117298 | 10/2008 |
| WO | 2008135980 | 11/2008 |
| WO | 2008136010 | 11/2008 |
| WO | 2009151899 | 12/2009 |
| WO | 2011039782 | 4/2011 |
| WO | 2012004801 | 1/2012 |
| WO | 2012015999 | 2/2012 |

OTHER PUBLICATIONS

"International Search Report for PCT/IN2012/000202 dated Aug. 30, 2012".

*Primary Examiner* — Bruck Kifle
(74) *Attorney, Agent, or Firm* — Kramer Amado, P.C.

(57) ABSTRACT

Disclosed is a process for the preparation of imatinib of formula (I), or its mesylate salt with controlled level of genotoxic impurity of formula (II), a key intermediate for imatinib.

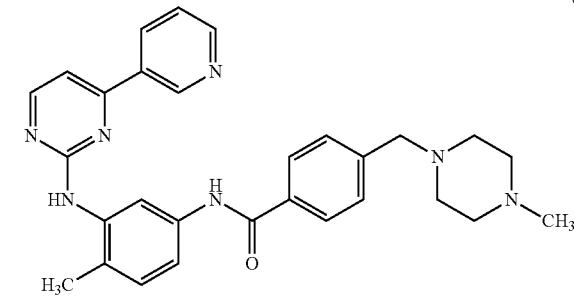

(I)

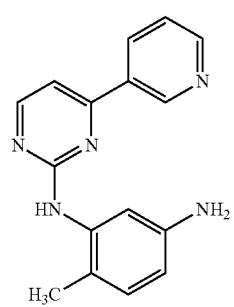

(II)

21 Claims, No Drawings

PROCESS FOR PREPARATION OF IMATINIB AND ITS MESYLATE SALT

FIELD OF THE INVENTION

The present invention relates to an improved and industrially advantageous process for the preparation of imatinib of formula I,

FORMULA I

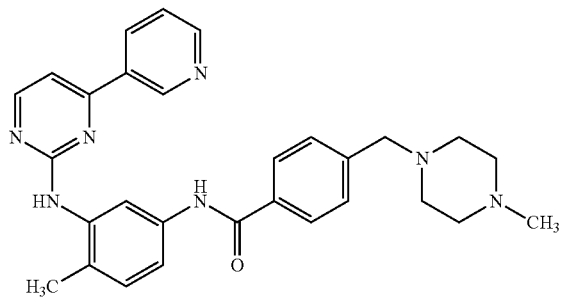

or its mesylate salt of formula Ia,

FORMULA Ia

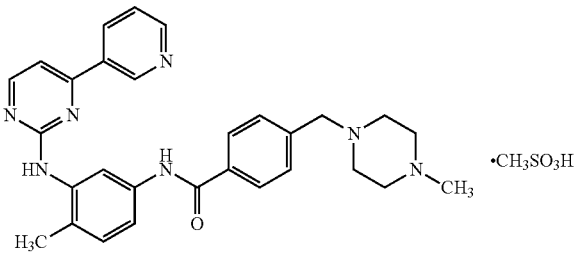

with controlled level of genotoxic impurities.

Further present invention relates to an efficient and reproducible process for the preparation of α-form of imatinib mesylate.

BACKGROUND OF THE INVENTION

Imatinib of formula I, functions as specific inhibitor of a number of tyrosine kinase enzymes and is chemically known as N-{5-[4-(4-methyl-piperazinomethyl)-benzoylamido]-2-methylphenyl}-4-(3-pyridyl)-2-pyrimidine-amine.

FORMULA I

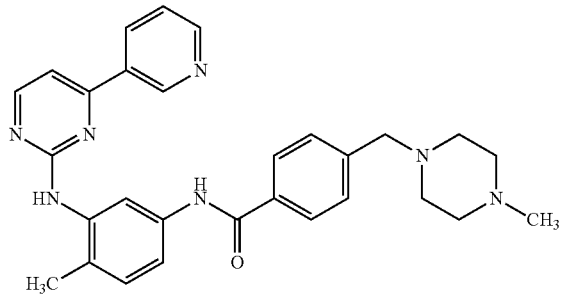

It is indicated for the treatment of chronic myeloid leukemia (CML), Philadelphia chromosome positive leukemia, for patients in chronic phase and in blast crisis, accelerated phase and also for malignant gastrointestinal stromal tumors. It selectively inhibits activation of target proteins involved in cellular proliferation. Imatinib also has potential for the treatment of other cancers that express these kinases, including acute lymphocytic leukemia and certain solid tumors. Imatinib is sold in U.S. by Novartis as Gleevec tablet containing imatinib mesylate equivalent to 100 or 400 mg of imatinib free base.

Imatinib and other related compounds were first disclosed in U.S. Pat. No. 5,521,184, wherein imatinib is prepared by involving amine intermediate of formula II, as shown below in scheme:

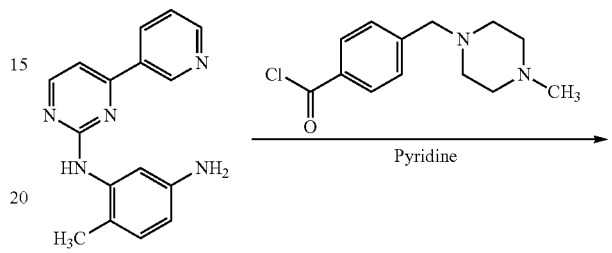

Formula II

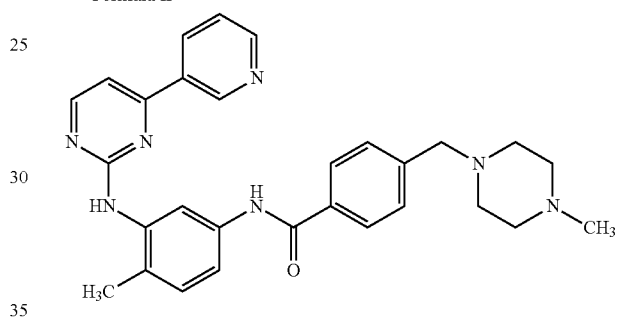

Imatinib is prepared by stirring a solution of amine intermediate of formula II with 1.14 meq (mol equivalent) of 4-(4-methylpiperazino methyl)benzoyl chloride in pyridine at room temperature for 23 hours to give crude product which is further slurried in dichloromethane/methanol and separated by column chromatography.

In our hands, we have found that crude product prepared by the above process; contain approximately 17 to 18% amine intermediate of formula II as an impurity which on chromatographic separation reduced to 0.08% (800 ppm). Use of column chromatography makes the process not suitable to employ for industrial synthesis being time consuming and tedious process. Even after performing tedious and time consuming chromatographic separation, amine intermediate of formula II which bears structural alerts, and is positive in several genotoxicity system still remain in the product up to 800 ppm as an impurity, which is unacceptable from regulatory requirements for genotoxic impurities.

Presence of amine intermediate of formula II as an impurity in the final product i.e. imatinib mesylate also yielded toxicological findings (hyperplasia, necrosis) in various organs in a 4-week study in rats. Such genotoxic compounds are believed to have potential to exert non-reversible changes in genetic material.

According to regulatory authorities, such as FDA, EU authorities, and in guidelines issued by ICH (The International Conference on Harmonization of Technical Requirements for Registration of Pharmaceuticals for Human Use), a drug manufacturer must submit data demonstrating that the product intended for marketing complies with regulations with regard to the content of impurities. The content of an unidentified impurity cannot exceed 0.1% (1000 ppm) by weight, while the amount of a known impurity cannot exceed 0.15% (1500 ppm). The drug manufacturer usually submits analytical data to the regulatory authority demonstrating that content of each impurity is in accordance with regulations. The regulatory authority checks the submitted data in order to ensure that the drug is having acceptable amount of impurities and is suitable for marketing. But this level of 0.1% (1000 ppm) or 0.15% (1500 ppm) may be even unacceptably high for an impurity if it is genotoxic.

According to a study carried out by Novartis, limit for this amine intermediate of formula II as an impurity in the final product can be 20 ppm based on technical feasibility. Further analysis results carried out on Gleevec tablet for quantification of amine intermediate shows its presence as 2-3 ppm.

The control of impurities bearing a genotoxic potential in pharmaceutical products has received more and more attention over the past years. As genotoxic impurities are considered to be harmful for the patient administrating the drug like imatinib mesylate, so these should be controlled at minimum possible level. Therefore synthetic process should be capable of producing imatinib mesylate with low amount of amine intermediate of formula II as an impurity.

There are several known processes reported for the preparation of imatinib and its mesylate salt but are either silent about the level of amine intermediate as an impurity in imatinib or yields the product with unacceptable amount of impurity.

U.S. Pat. No. 7,507,821 discloses preparation of imatinib by stirring a mixture of amine intermediate of formula II with 1.23 mole equivalent of 4-(4-methylpiperazino methyl)benzoyl chloride in pyridine at 50° C. for 4.5 hours to give imatinib which is slurried one or more times in ethyl acetate to yield imatinib of 97% purity. Use of pyridine makes the process disadvantageous as it is difficult to remove residual traces from final product.

U.S. Pat. No. 7,550,591 discloses a process for preparation of imatinib by stirring amine intermediate of formula II and 1.11 mole equivalent (meq) of 4-(4-methylpiperazino methyl)benzoic acid in tetrahydrofuran and water for 20 minutes followed by addition of 1-ethyl-3-(3-dimethyllaminopropyl) carbodiimide hydrochloride and then further stirring for one hour to give imatinib which is then purified to give product having amine intermediate 0.01% (100 ppm). Presence of unacceptable amount of the genotoxic impurity i.e. amine intermediate of formula II makes the process not amenable for regulatory market.

U.S. Pat. No. 7,638,627 discloses a process for preparation of imatinib by suspending amine intermediate of formula II in dimethylformamide followed by addition of 1.28 meq of 4-(4-methylpiperazino methyl)benzoyl chloride dihydrochloride and heating at 70° C. for 15 hours to give imatinib trihydrochloride monohydrate followed by basification with aqueous ammonia to give imatinib. Process involves an extra step of generation of trihydrochloride salt and then its neutralization to give imatinib free base.

US patent application 2008/0103305 discloses preparation of imatinib by adding 1.1 meq of 4-(4-methylpiperazino methyl)benzoyl chloride dihydrochloride to a solution of amine intermediate of formula II in pyridine followed by stirring at 15-20° C. for 1 hour and heating to 40° C. to give imatinib of purity more than 98%. Use of pyridine makes the process disadvantageous as it is difficult to remove residual traces from final product and process silent about the presence or absence of genotoxic impurity.

PCT publication WO 2008/24829 discloses preparation of imatinib by condensation of amine intermediate of formula II with 1.11 mole equivalent of 4-(4-methylpiperazino methyl) benzoyl chloride dihydrochloride in the presence of anhydrous pyridine at 20° C. for 18 hours to give imatinib which was further purified with silica gel chromatography.

PCT publication WO 2008/0117298 discloses preparation of imatinib by the reaction of amine intermediate of formula II with 1.22 meq of 4-(4-methylpiperazino methyl)benzoyl chloride dihydrochloride in the presence of base to form imatinib which is then washed with isopropanol, suspended in water followed by extraction with chloroform, distillation and treatment of residue with ethyl acetate give imatinib.

PCT publication WO 2008/136010 discloses a process for the preparation of imatinib by reaction of amine intermediate of formula II with 0.57 meq of 4-(4-methylpiperazino methyl)benzoyl chloride in chloroform and potassium hydroxide at 25-35° C. for 4 hours to give imatinib.

Most of the prior art processes are silent about amount of genotoxic impurity i.e. amine intermediate of formula II in final product. It is observed that when amine intermediate of formula II is reacted with 4-(4-methylpiperazino methyl)benzoic acid or reactive derivatives or their salts with molar ratio of amine intermediate to benzoic acid or its derivative in the range of 1:1 to 1:1.30, it finally results in imatinib mesylate having genotoxic amine intermediate of formula II more than 100 ppm, which is not acceptable.

In addition to concern of genotoxic impurity, prior art processes for the synthesis of α-form of imatinib mesylate does not produce reproducible results.

U.S. Pat. No. 6,894,051 ('051) discloses preparation of imatinib mesylate in two crystalline forms such as α-crystal form and β-crystal form. U.S. '051 patent describes α-crystal form of imatinib mesylate characterized by needle shaped crystals and hygroscopic nature, which make it unsuitable for pharmaceutical formulation as solid dosage forms. Patent discloses a process for preparing the α-crystal form wherein imatinib base was suspended in ethanol; methane sulfonic acid was added and heated under reflux for 20 minutes and than filtered at 65° C. The filtrate was evaporated down to 50% and the residue filtered off at 25° C. The mother liquor was evaporated to dryness. Both residues were suspended in ethanol and dissolved under reflux with addition, of water, cooling overnight to 25° C., filtration and drying yielded imatinib mesylate α form. The above mentioned process does not give reproducible results due to its cumbersome nature and always results in mixture of forms α and β form.

Various other references like U.S. Pat. No. 7,732,601, US patent application nos. 2006/0223816, 2007/0265288, 2008/0255138, 2008/0090833; PCT publication nos. 2006/048890, 2009/151899; an Indian application no. 216/KOLNP/2009 etc. discloses process for the preparation of α-form of imatinib mesylate. It has been noticed that polymorphic α form of imatinib mesylate when prepared as per the process reported in the prior art is not isolated in pure form it is contaminated with other forms such as β form or found to have residual solvent in unacceptable amounts.

Further prior art processes are associated with one or more disadvantages such as use of pyridine, chromatographic techniques, low purity of imatinib, inconsistency in yielding α-form. In view of the above, there exists a need for an improved process for preparing imatinib mesylate which yields the product containing acceptable levels of genotoxic impurity, i.e., less than 20 ppm, as required by the regulatory authorities. There is also a need to develop an a reproducible and improved process wherein α form of imatinib mesylate is isolated consistently in pure form without contamination of other forms and have residual solvents in specified limits.

Therefore, present invention fulfill the need in the art and provides a process for preparation of imatinib or its mesylate salt that circumvent disadvantages associated with prior art, proved to be advantageous from industrial point of view and also fulfill purity criteria's led by various regulatory authorities. Present invention also provides an efficient and reproducible process for the preparation of α-form of imatinib mesylate using new solvent system.

OBJECTIVES OF THE INVENTION

The foremost objective of the present invention is to provide an improved and advantageous process for preparation of imatinib mesylate which fulfill purity criteria led by various regulatory authorities.

Another objective of the present invention is to provide a process for preparation of highly pure imatinib mesylate having genotoxic amine impurity of formula II less than 20 ppm.

Still another objective of the present invention is to provide a process for preparation of highly pure imatinib or its mesylate salt by optimizing reaction variables, specifically molar ratio.

Yet another objective of present invention is to provide a reproducible process for the preparation of α-form of imatinib mesylate.

SUMMARY OF THE INVENTION

Accordingly, present invention provides a process for the preparation of an improved and advantageous process for the preparation of imatinib mesylate of formula Ia, FORMULA Ia

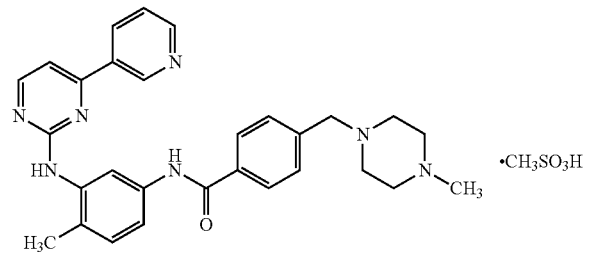

having acceptable level of amine intermediate of formula II,

FORMULA II

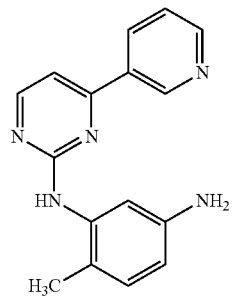

According to one embodiment, present invention provides an improved process for the preparation of imatinib mesylate, comprising the steps of:

a). reacting amine intermediate of formula II,

FORMULA II

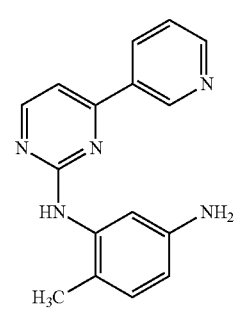

with intermediate of formula III

FORMULA III

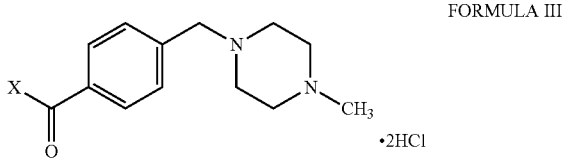

wherein X is selected from —OH, halogen or a good leaving group
in the presence of a suitable base in an organic solvent,
wherein molar ratio of amine intermediate of formula II to intermediate of formula III is 1:>1.5;
b). isolating imatinib of formula I from the reaction mixture; and
c). optionally, purifying imatinib of formula I.

According to one embodiment, present invention provides an improved process for the preparation of imatinib mesylate having amine intermediate less than 20 ppm., comprising the steps of:

a). reacting amine intermediate of formula II,

FORMULA II

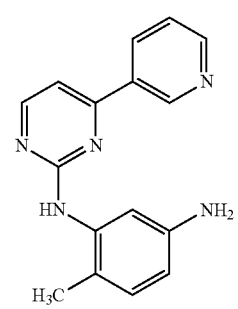

with intermediate of formula III

FORMULA III

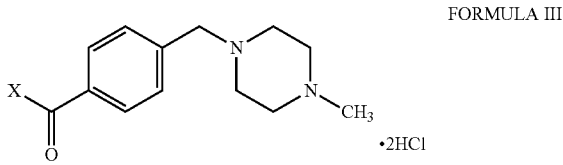

wherein X is selected from —OH, halogen or a good leaving group
in the presence of a suitable base in an organic solvent, wherein molar ratio of amine intermediate of formula II to intermediate of formula III is 1:>1.5;

b). isolating imatinib of formula I from the reaction mixture;

c). optionally, purifying imatinib of formula I; and d). reacting imatinib with methanesulfonic acid to form imatinib mesylate.

According to other embodiment, present invention provides a process for the preparation of imatinib or pharmaceutically acceptable salts thereof, comprising the steps of:

a). admixing intermediate of formula III in a suitable solvent with a suitable base;

b). reacting the same with amine intermediate of formula II, wherein molar ratio of amine intermediate of formula II to intermediate of formula III is about 1:>1.5 to form imatinib of formula I;

c). isolating imatinib of formula I; and d). optionally, purifying imatinib of formula I.

According to another embodiment, present invention provides a process for the preparation of pure α form of imatinib mesylate, comprising the steps of:

a). combining imatinib and dimethylsulfoxide;

b). adding methanesulfonic acid to the resulting mixture;

c). adding a second solvent with optional seeding;

d). stirring the reaction mixture for a time sufficient till complete precipitation; and e). isolating α form of imatinib mesylate there from.

Accordingly, in one general aspect there is provided pure α form of imatinib mesylate.

Embodiments of pure α form of imatinib mesylate may include one or more of the following features. For example, α form of imatinib mesylate may have no detectable quantity of other polymorphic forms of imatinib mesylate. α form of imatinib mesylate may have 2% or less of other polymorphic forms of imatinib mesylate.

DETAILED DESCRIPTION OF THE INVENTION

As used herein, term "meq" refers to mole equivalent i.e. molar ratio of one reactant with respect to other reactant used for the reaction.

As used herein term "ppm" refers to parts per million

As used herein term "amine intermediate or amine impurity" refers to amine intermediate of formula II.

As used herein "pure α-form" refers to α form of imatinib mesylate having 2% or less of other polymorphic forms of imatinib, preferably no detectable quantity of other polymorphic forms of imatinib mesylate.

The present invention provides a process for the preparation of imatinib or pharmaceutically acceptable salts thereof containing controlled level of genotoxic amine intermediate of formula II. Particularly present invention provides a process for the preparation of imatinib mesylate having less than 20 ppm of genotoxic amine intermediate of formula II, preferably less than 10 ppm.

According to one embodiment, present invention provides a process for the preparation of imatinib by reaction of amine intermediate of formula II with more than 1.5 meq of intermediate of formula III.

Generally, process involves reaction of amine intermediate of formula II with intermediate of formula III in the presence of a suitable base in an organic solvent at a temperature of 0 to reflux temperature for 0.5 to 15 hours. Suitable base used for reaction includes organic or inorganic base. Organic base can be selected from primary, secondary or tertiary amine such as triethylamine, diisopropylethylamine and the like. Inorganic base includes alkali or alkaline metal hydroxide, carbonate, bicarbonate, alkoxide and the like such as potassium carbonate, sodium bicarbonate and the like. Organic solvent can be selected from but not limited to halogenated solvent such as dichloromethane, chloroform; ketones such as acetone; alcohol such as isopropanol; ether such as tetrahydrofuran; aprotic solvent such as dimethylformamide, N-methylpyrrolidone and the like or mixture thereof. Usually reaction can be carried out at a temperature of 5° C. to reflux temperature of solvent for 2 to 10 hours. Mol ratio of intermediate of formula II to intermediate of formula III used for the reaction ranges from 1:>1.5 preferably 1:1.5-2.5. Reaction completion can be monitored by suitable chromatographic techniques such as high pressure liquid chromatography (HPLC), ultra pressure liquid chromatography (UPLC), thin layer chromatography (TLC) and the like. After completion of reaction, imatinib can be isolated from reaction mixture by using a suitable technique known in the art. Preferably, imatinib can be isolated from reaction mixture after employing acid base treatment to the reaction mass. Reaction mass can be acidified with a suitable acid selected from hydrochloric acid, acetic acid, formic acid and the like followed by layer separation. Resulting aqueous layer can be washed with a suitable solvent selected from halogenated solvent such as dichloromethane, chloroform and the like. Aqueous layer is then diluted with a suitable solvent selected from ether such as tetrahydrofuran; nitrile such as acetonitrile; ketone such as acetone; $C_{1-3}$ alcohol and the like or mixture thereof followed by basification with a suitable base to precipitate the desired compound. Suitable base includes inorganic base selected from alkali or alkaline hydroxide, carbonate or bicarbonate thereof such as sodium hydroxide, potassium hydroxide and the like; or organic base such as ammonium hydroxide, diisopropylethylamine, triethylamine and the like. Desired product can be isolated from the reaction mixture by suitable techniques such as filtration, decantation or centrifugation and the like. Imatinib thus isolated can be optionally washed with an aqueous solution of suitable base and/or water.

The order and manner of combining the reactants at any stage of the process are not important and may be varied. The reactants may be added to the reaction mixture as solids, or may be dissolved individually and combined as solutions. Further, any of the reactants may be dissolved together, or their solutions may be combined in any order.

Amine intermediate of formula II can be added to intermediate of formula III or they can be added in reverse order or alternatively can be combined together. Mode of addition does not make any impact on the yield and purity of the product.

Preferably, amine intermediate of formula II can be added to a solution of intermediate of formula III in a suitable base and solvent to form imatinib. Intermediate of formula III can be first treated with a suitable base in a suitable solvent at a temperature of 10 to 40° C. for 0.5 to 2 hours, prior to the reaction with amine intermediate of formula II. Thereafter, reaction mixture can be reacted with amine intermediate of formula II to yield imatinib having low level of genotoxic amine intermediate of formula II.

The imatinib free base, thus obtained, can optionally be purified by the conventional methods such as precipitation, crystallization or slurrying, washing in a solvent, solvent employed for the purification includes water, ester such as ethyl acetate, n-propyl acetate; ether such as diethyl ether, tetrahydrofuran, diisopropyl ether, methyl tertiary butyl ether; alcohol such as methanol, isopropanol, ethanol; ketone such as acetone, methyl isobutyl ketone; hydrocarbon such as n-hexane, toluene, xylene, halogenated solvent such as dichloromethane; nitrile solvent such as acetonitrile, and the like or mixture thereof. The solid product can be recovered by suitable techniques such as decantation, filtration by gravity or by suction, centrifugation and the like.

Imatinib, prepared by the above process, is found to be highly pure and contain amine intermediate of formula II less than 50 ppm, preferably less than 30 ppm, more preferably 10 ppm. It is found by present inventor that using intermediate of formula III in amount more than 1.5 meq as compared to amine intermediate of formula II reduce level of amine intermediate in the final product. In order to satisfy the requirements of various regulatory bodies for minimal impurities in an active pharmaceutical ingredient (API), it is important to synthesize imatinib using a process that minimizes the amount of impurities including genotoxic impurity, produced during the various synthetic steps. During optimization of the process, it has been found that molar ratio of the reactant is very critical reaction variable for obtaining the imatinib with acceptable level of genotoxic impurity i.e. amine intermediate of formula II, which is difficult to remove once it remain in imatinib.

Imatinib free base may be converted to pharmaceutically acceptable salts of imatinib by methods already known in the art. Pharmaceutically acceptable acids used for the salt formation includes inorganic acid such as hydrochloric acid, hydrobromic acid; organic acid includes acetic acid, tartaric acid, formic acid, citric acid, oxalic acid, methansulfonic acid and the like. Preferably, imatinib mesylate is prepared.

Imatinib can be converted to imatinib mesylate by any method known in the art or by the method as described herein. Imatinib having less than 50 ppm of amine intermediate of formula II yield imatinib mesylate having less than 20 ppm of amine intermediate, preferably less than 5 ppm; more preferably 1.6 ppm. Imatinib base prepared by the process of present invention can be converted to imatinib mesylate α-form, β-form, amorphous, or any other polymorph or mixture of forms.

According to another embodiment, present invention provides an efficient and reproducible process for the preparation of α-form of imatinib mesylate.

Generally, process involves treatment of imatinib in dimethylsulfoxide with methanesulfonic acid at a temperature of 5 to 80° C. for few minutes to few hours, preferably 25 to 30° C. for 5 minutes to 1 hour. Mixture of imatinib in dimethylsulfoxide and methanesulfonic acid can be heated to the reflux temperature of solvent or till dissolution depending upon the solubility of imatinib. The reaction mixture can optionally be filtered to remove any insoluble particulate present in the reaction mixture, when reaction mixture is completely soluble dimethylsulfoxide. Reaction mixture can be optionally cooled to 5° C. to ambient temperature. Methanesulfonic acid used for the reaction can be used as such or in solution with dimethylsulfoxide.

Thereafter, a second solvent can be added to the resulting mixture with optional seeding. Second solvent can be selected from the group consisting of alcohol such as 2-propanol, 1-propanol, butanol; ester such as ethyl acetate, methyl acetate, propyl acetate; ketone such as acetone, methylisobutyl ketone, methyl ethyl ketone; aliphatic hydrocarbon such as n-heptane, cyclohexane; halogenated solvent such as dichloromethane, chloroform; ether such as tetrahydrofuran, isopropyl ether; nitrile such as acetonitrile; aprotic solvent such as dimethylsulfoxide and the mixture thereof. Second solvent can be used as a single solvent or mixture of two or more in any proportion.

Reaction mixture can be optionally seeded with α-crystalline form of imatinib mesylate. The seeding compound can be added after the addition of second solvent to the resulting mixture or it can be added prior to addition of second solvent to reaction mixture. In another alternate way, a mixture of second solvent with seeding compound can be prepared by mixing second solvent with seeding compound with optional stirring and then added to the reaction mixture. In another way, seeding compound and second solvent can be added simultaneously to the reaction mixture. As the order of adding second solvent and seeding compound does not have any impact on the quality as well as quantity of the resulting α-crystalline form of imatinib mesylate, so it can be added in any order or in mixture.

After the addition of second solvent with optional seeding, reaction mixture can be stirred for few minutes to few hours at a temperature of 20 to 60° C., preferably for 25 to 55° C. More preferably mixture can be stirred till the complete precipitation of the α-crystalline form of imatinib mesylate take place. Mixture can be optionally cooled to a temperature of 15 to ambient temperature and further stirred till for 1 to 15 hours, preferably 2 to 8 hours. The resulting product can be isolated from the reaction mixture by suitable techniques such as filtration, centrifugation or decantation and the like.

α-Crystalline form of imatinib mesylate thus obtained can be optionally washed with a suitable solvent selected from the solvents as used for the process.

Imatinib mesylate, prepared by the using the imatinib synthesized by the process of present invention, is found to be highly pure and contain amine intermediate of formula II less than 20 ppm, preferably less than 10 ppm, more preferably 1.6 ppm. Imatinib mesylate is having purity more than 99% by HPLC, preferably 99.5% by HPLC.

The starting material amine intermediate of formula II can be procured from the commercial sources or can be prepared by the methods already known in the art.

Similarly, intermediate of formula III can be procured from the commercial sources or can be prepared by the methods already known in the art or can be prepared by the method as described herein for the reference.

Intermediate of formula III (wherein X is as defined above provided X is not —OH group) can be prepared by the activation of corresponding dihydrochloride salt of acid intermediate.

Generally, process involves the reaction of acid intermediate of formula III (wherein in X is —OH) with a suitable activating agent at a temperature of 20 to 80° C. for 2 to 20 hours. Preferably reaction can be carried out at a temperature of 40 to 75° C. till the completion of the reaction. Suitable activating agent which includes thionyl halide such as thionyl chloride; oxalyl chloride, phosphorus oxychloride; and the like. Reaction can be carried out in a suitable solvent for providing reaction media and can be selected from aliphatic or aromatic hydrocarbon such as toluene; halogenated solvent such as dichloromethane, chloroform and the like. Reaction can be advantageously carried out using a catatalytic amount of N,N-dimethylformamide when activating reagent used is thionyl halide. After the completion of reaction, desired intermediate can be isolated from the reaction mixture or can be used in situ for the further reaction. Intermediate of formula III (wherein X is as defined above provided X is not —OH group) can be isolated by employing suitable techniques such as filtration, centrifugation or decantation. Major advantages of the present invention lie in high purity of imatinib and as well as of imatinib mesylate with minimum level of genotoxic amine intermediate. Another advantage of the present invention is that it provides a process for the preparation of imatinib mesylate having controlled level of amine intermediate, preferably less than 20 ppm, more preferably less than 5 ppm. The present invention also avoids the formation of genotoxic impurities during the synthesis of imatinib in order to circumvent its carry forward to imatinib mesylate. Still another advantage of present invention is to provide an efficient and reproducible process for the preparation of α-form of imatinib mesylate. Also the product obtained is having acceptable limits of residual solvent. α-form of imatinib mesylate of the present invention has 2% or less of other polymorphic forms of imatinib mesylate. More preferably α form of imatinib mesylate has no detectable quantity of any other known polymorphic form of imatinib mesylate. The last but not the least advantage of the process is to provide imatinib or its mesylate salt which complies with the regulatory requirement Although, the following examples illustrate the practice of the present invention in some of its embodiments, the examples should not be construed as limiting the scope of the invention.

Other embodiments will be apparent to one skilled in the art from consideration of the specification and examples. It is intended that the specification, including the examples, is considered exemplary only, with the scope and spirit of the invention being indicated by the claims, which follow.

EXAMPLES

Reference Example 1

Preparation of Imatinib as Per Process Given in U.S. Pat. No. 5,521,184

A mixture of 4-methyl-N-(4-pyridin-3-yl-pyridin-2-yl) benzene-1,3-diamine (10 g), pyridine (400 ml) and 4-(4-methyl-piperazin-1-ylmethyl)-benzoyl chloride (13.4 g) were stirred for 23 hours at room temperature. The reaction mixture was concentrated under HV. Water (250 ml) was added to the resulting reaction mass, cooled to 0° C. and filtered. Resulting product was dried at 80° C. under vacuum, slurried with chloroform/methanol (95:5) and filtered to give title compound having purity 80.5% and amine intermediate: 18.3% by HPLC.

Reference Example 2

Preparation of Imatinib as Per Process Given in WO 2008/117298

4-(4-Methyl-piperazin-1-ylmethyl)-benzoylchloride dihydrochloride (7.2 g) was suspended in isopropanol (100 ml) followed by addition of potassium carbonate (5.3 g). Mixture was stirred for 30 minutes at room temperature. The resulting mixture was treated with 4-methyl-N-(4-pyridin-3-yl-pyridiin-2-yl)benzene-1,3-diamine (5 g) and slurry was refluxed for 1 hour. After completion of reaction (monitored by TLC till absence of the amine), mixture was filtered and washed with hot isopropanol (30 ml). Resulting product was suspended in water (100 ml) extracted with chloroform (2×100 ml). Organic layer was distilled under vacuum to form a residue which was treated with ethyl acetate (50 ml). Resulting slurry was filtered and dried to give title compound having purity 98.2% by HPLC; amine intermediate: 750 ppm.

Example 1

Preparation of Imatinib

Step I: Preparation of 4-(4-methylpiperazin-1-ylmethyl)benzoyl chloride dihydrochloride A mixture of 4-(4-methylpiperazin-1-ylmethyl) benzoic acid dihydrochloride (150 g), thionyl chloride (600 ml) and N,N-dimethylformamide (37.2 ml) was refluxed for 20 hours. After completion of reaction, the reaction mass was distilled out completely under vacuum to give residue which was diluted with dichloromethane (300 ml). The solid thus precipitated was filtered and washed to give 135 g of the title compound.

Step II: Preparation of Imatinib

To a mixture of 4-(4-methylpiperazin-1-ylmethyl)benzoyl chloride dihydrochloride in dichloromethane (1.5 L), potassium carbonate (240 g) was added at ambient temperature and stirred for 30 minutes. The reaction mass was cooled to 0-5° C. and 4-methyl-N-(4-pyridin-3-yl-W pyridin-2-yl)benzene-1,3-diamine (60 g) was added to the reaction mixture. Reaction mass was refluxed for 10 hours. After completion of reaction, the reaction mass was quenched with dilute hydrochloric acid (1.26 L) up to pH 2.5-3.0 and layers were separated. Aqueous layer was washed with dichloromethane and diluted with tetrahydrofuran (360 ml). Resulting reaction mixture was basified up to pH 8.0-8.5 with aqueous sodium hydroxide solution (20%, 600 ml). Solid thus precipitated was filtered, washed with sodium hydroxide solution and demineralised water to give title compound having amine intermediate: 13.3 ppm.

Resulting product was dissolved in a mixture of dichloromethane (480 ml) and methanol (120 ml), washed with water and concentrated to give residue. Methanol (1.2 L) was added to the resulting residue, refluxed and charcoalized. Methanol was partially distilled out from the reaction mixture and cooled down to 25-30° C. and stirred for 1.0 hour. Solid thus obtained was filtered, washed and dried to give 79 g (74%) of title compound having purity 99.97% by HPLC and amine intermediate: 2.6 ppm.

Example 2

Preparation of Imatinib

A mixture of 4-(4-methylpiperzin-1-ylmethyl)benzoic acid dihydrochloride (2.5 kg), thionyl chloride (16.2 kg) and N,N-dimethylformamide (0.62 L) was refluxed for 20 hours. After completion of reaction, the reaction mass was distilled out completely under vacuum to give residue which was diluted with dichloromethane (5.0 L). Solid thus precipitated was filtered and washed to give 4-(4-methylpiperzin-1-ylmethyl)benzoyl chloride dihydrochloride. Dichloromethane (25.0 L), potassium carbonate (4 kg) was added to the above product and stirred for 30 minutes. The reaction mass was cooled to 0-5° C. and 4-methyl-N-(4-pyridin-3-yl-pyridin-2-yl)benzene-1,3-diamine (1.0 kg) was added to the reaction mixture. The reaction mass was refluxed for 10 hours. After completion of reaction, the reaction mass was quenched with dilute hydrochloric acid (21.0 L) up to pH 2.5-3.0 and layers were separated. Aqueous layer was washed with dichloromethane, diluted with tetrahydrofuran (6.0 L) and basified up to pH 8.0-8.5 with aqueous sodium hydroxide solution (20%, 10.0 L). Solid thus precipitated was filtered, washed with sodium hydroxide solution and demineralised water to give title compound having amine intermediate 29 ppm. Resulting solid was dissolved in a mixture of dichloromethane and methanol (8.0 L+2.0 L), washed with water and concentrated to give residue: Methanol (20.0 L) was added to the resulting residue, refluxed and charcoalized. Methanol was partially distilled out and resulting reaction mass was cooled down to 25-30° C. Reaction mixture was stirred for 1.0 hour. Reaction mixture was filtered, washed and dried to give 1.3 kg (yield: 73%) of title compound having purity 99.8% by HPLC and amine intermediate: 9.0 ppm.

Example 3

Preparation of Imatinib

A mixture of 4-(4-methylpiperazin-1-ylmethyl)benzoic acid dihydrochloride (50 g), thionyl chloride (200 ml) and N,N-dimethylformamide (12.5 ml) was refluxed for 20 hours. After completion of reaction, the reaction mass was distilled out completely under vacuum to give residue which was diluted with dichloromethane (100 ml). Solid thus precipitated was filtered and washed to give 4-(4-methylpiperazin-1-ylmethyl)benzoyl chloride dihydrochloride. To a mixture of 4-Methyl-N-(4-pyridin-3-yl-pyridin-2-yl)benzene-1,3-diamine (20 g) in dichloromethane (500 ml), potassium carbonate (80 g) was added and stirred for 30 minutes. 4-(4-methylpiperazin-1-ylmethyl)benzoyl chloride dihydrochloride (prepared above) was added to the reaction mass at 0-5° C. and refluxed for 10 hours. After completion of reaction, reaction mass was quenched with dilute hydrochloric acid (420 ml) up to pH 1.0-3.0 and layers were separated. Aqueous layer was washed with dichloromethane, diluted with tetrahydrofuran (120 ml) and basified up to pH 8.0-8.5 with 10% sodium hydroxide solution (200 ml). Solid thus precipitated was filtered, washed with sodium hydroxide solution and demineralised water to give title compound having amine intermediate: 39.7 ppm).

Example 4

Preparation Imatinib Mesylate

Method A:
To a mixture of imatinib (20 g, having amine impurity: 30 ppm) in dimethylsulfoxide (40 ml), methanesulfonic acid (4 g) was added and heated to 40-45° C. till clear solution. Solution was filtered and washed with dimethylsulfoxide (4 ml). A part of resulting solution (15 ml) was added to a mixture of isopropanol and dimethylsulfoxide (60 ml) at 50 to 60° C. followed by seeding with α-form of imatinib mesylate. Reaction mixture was stirred for 15 minutes followed by addition of remaining filtered solution and stirred for 2 hour at 50-60° C. The reaction mass was cooled to 20-25° C., stirred and filtered. Product thus filtered and washed with isopropanol (20 ml) and dried to give 21 g (88%) of title compound having purity: 99.8% by HPLC; amine impurity: 4.65 ppm.

Method B:
To a mixture of imatinib (5 g, having amine impurity: 6.7 ppm) in dimethylsulfoxide (10 ml), methanesulfonic acid (1 g) was added and heated to 40-45° C. till clear solution. Solution was filtered and washed. To a mixture of isopropanol, ethyl acetate and n-propanol (50 ml+25 ml+25 ml), seeding material of α-form was added and the stirred for 30 minutes (seeding mixture). Filtered solution obtained above was added to seeding mixture at 20-25° C. and stirred for 5 hours. Solid thus formed was filtered, washed and dried to give 5.2 g (87%) of title compound having purity: 99.76% by HPLC; amine intermediate: <1.0 ppm.

Method C:
To a stirred suspension of imatinib (10 g, having amine impurity: 7.2 ppm) in a mixture of acetonitrile (20 ml) and demineralized water (10 ml), methansulfonic acid (2 g) was added to get clear solution. Reaction mixture was charcoalised and filtered. Acetonitrile (200 ml) was added to the reaction mixture at 25-30° C. The resulting mixture was filtered, washed with acetonitrile and dried to give 1 Og (84%) of the title compound having purity 99.8% by HPLC; amine intermediate: 1.6 ppm.

Example 5

Preparation of β-Form of Imatinib Mesylate

To a stirred suspension of imatinib (5 g) in tetrahydrofuran (20 ml) and water (10 ml), methanesulphonic acid (0.97 gl) was added to get clear solution. Reaction mixture was charcoalised and filtered. Tetrahydrofuran (75 ml) was added slowly to the reaction mixture at 25-30° C. The resulting mixture was filtered, washed with t-butylmethyl ether and dried to give 5.2 g of the title compound having purity 99.68% by HPLC.

Example 6

Preparation of α-Form of Imatinib Mesylate

To a mixture of imatinib (10 g) in dimethylsulfoxide (50 ml), methanesulfonic acid (2 g) was added at ambient temperature and reaction mixture was heated to 45° C. to get clear solution. Reaction mixture was filtered. 10-15% of resulting filtered solution was added to isopropanol (210 ml) at 55-60° C. and stirred for 15 minutes. Seeding of α-form (0.2 g) was added to this solution followed by the addition of remaining filtered solution and mixture was stirred for 2.0 hours at 55 to 60° C. The reaction mass was cooled to 20-25° C. and stirred for another 2 hours at 20 to 25° C. Reaction mass was filtered, washed and dried to give 9.8 g of title compound having DSC: 226° C.

Example 7

Preparation of α-Form of Imatinib Mesylate

Imatinib (100 g) was suspended in dimethylsulfoxide (180 ml) and methanesulfonic acid (20 g) was added to mixture at 25 to 30° C. Reaction mass was heated to 45° C. till clear solution and filtered. 10% of filtered solution was added to a mixture of isopropanol (900 ml), ethyl acetate (600 ml) and n-propanol (600 ml) and dimethylsulfoxide (300 ml) at 20° C. followed by seeding and stirred for 30 minutes. Remaining filtered solution was added to above suspension and stirred for 5.0 hours at 20-25° C. Reaction mass was filtered, washed and dried to 102 g of α-form of imatinib mesylate.

We claim:
1. A process for the preparation of imatinib mesylate of formula Ia, comprising:

a) reacting an amine intermediate of formula II

FORMULA II with an intermediate of formula III in the presence of a base in an organic solvent, in a ratio of at least 1.5 molar equivalents of the intermediate of formula III per molar equivalent of the intermediate of formula II;

FORMULA III wherein X is selected from the group consisting of —OH and halogen;

b) isolating imatinib of formula I from the reaction mixture,

FORMULA I wherein said imatinib of formula I contains less than 50 ppm of the amine intermediate of formula II;

c) optionally, purifying imatinib of formula I; and d) reacting imatinib with methanesulfonic acid to form imatinib mesylate of formula Ia, wherein said imatinib mesylate produced in step (d) contains less than 20 ppm of the intermediate of formula II.

2. The process according to claim 1, wherein, in step a), the base is an organic base or an inorganic base.

3. The process according to claim 2, wherein the organic base is selected from the group consisting of primary amines, secondary amines, and tertiary amines.

4. The process according to claim 2, wherein the inorganic base is selected from the group consisting of:
   at least one alkali metal, hydroxide, carbonate, bicarbonate, or alkoxide;
   at least one alkaline metal hydroxide, carbonate, bicarbonate, or alkoxide; and
   a mixture thereof.

5. The process according to claim 1, wherein, in step a), the organic solvent is selected from the group consisting of halogenated solvents, ketone solvents, alcohol solvents, ether solvents, aprotic solvents, and mixtures thereof.

6. The process according to claim 1, wherein, in step a), the organic solvent is selected from the group consisting of dichloromethane, chloroform, acetone, isopropanol, tetrahydrofuran, dimethylformamide, N-methylpyrrolidone and mixtures thereof.

7. The process according to claim 1, wherein step a) comprises reacting one molar equivalent of an amine intermediate of formula II with from 1.5 molar equivalents of an intermediate of formula III to 2.5 molar equivalents of an intermediate of formula III.

8. A process for the preparation of imatinib, comprising:

a) admixing an intermediate of formula III with a base and an organic solvent to form a reaction mixture;

FORMULA III wherein X is selected from the group consisting of —OH and halogen;

b) reacting the intermediate of formula III in the reaction mixture with an amine intermediate of formula II,

FORMULA II wherein at least 1.5 molar equivalents of the intermediate of formula III is used per molar equivalent of the intermediate of formula II; and c) isolating imatinib of formula I from the reaction mixture;

FORMULA I wherein said imatinib of formula I contains less than 50 ppm of the amine intermediate of formula II; and d) optionally, purifying imatinib of formula I.

9. The process according to claim 8, wherein, in step a), the base is an organic base or an inorganic base.

10. The process according to claim 9, wherein the organic base is selected from the group consisting of primary amines, secondary amines, and tertiary amities.

11. The process according to claim 9, wherein the inorganic base is selected from the group consisting of:
   at least one alkali metal hydroxide, carbonate, bicarbonate, or alkoxide;
   at least one alkaline metal hydroxide, carbonate, bicarbonate, or alkoxide; and
   a mixture thereof.

12. The process according to claim 8, wherein, in step a), the organic solvent is selected from the group consisting of halogenated solvents, ketone solvents, alcohol solvents, ether solvents, aprotic solvents, and mixtures thereof.

13. The process according to claim 8, wherein, in step a), the organic solvent is selected from the group consisting of dichloromethane, chloroform, acetone, isopropanol, tetrahydrofuran, dimethylformamide, N-methylpyrrolidone and mixtures thereof.

14. The process according to claim 8, wherein step b) comprises reacting one molar equivalent of an amine intermediate of formula II with from 1.5 molar equivalents of an intermediate of formula III to 2.5 molar equivalents of an intermediate of formula III.

15. The process according to claim 8, further comprising: reacting imatinib with methanesulfonic acid to form imatinib mesylate.

16. The process according to claim 15, wherein said imatinib mesylate contains less than 20 ppm of the amine intermediate of formula II.

17. A process for the preparation of an α form of imatinib mesylate,
   said α form having 2% or less of other polymorphic forms,
   said α form showing a thermal event by DSC at 226° C.;
   said method comprising the steps of:
   a) combining imatinib and dimethylsulfoxide;
   b) adding methanesulfonic acid to the resulting mixture;
   c) adding a second solvent with optional seeding;
   d) stirring the reaction mixture for a time sufficient till complete crystallization; and
   e) isolating α form of imatinib mesylate therefrom.

18. The process according to claim 17, wherein, in step c), the second solvent is selected from the group consisting of alcohol solvents, ester solvents, ketone solvents, aliphatic hydrocarbon solvents, halogenated solvents, ether solvents, nitrile solvents, aprotic solvents, and mixtures thereof.

19. The process according to claim 17, wherein, in step c), the second solvent is selected from the group consisting of 2-propanol, 1-propanol, butanol, ethyl acetate, methyl acetate, propyl acetate, acetone, methylisobutyl ketone, methyl ethyl ketone, n-heptane, cyclohexane, dichloromethane, chloroform, tetrahydrofuran, isopropyl ether, acetonitrile, dimethylsulfoxide and mixtures thereof.

20. The process according to claim 17, wherein, in step c), the second solvent is 2-propanol.

21. The process according to claim 17, wherein said α form of imatinib mesylate contains less than 20 ppm of a compound of formula II:

FORMULA II

* * * * *